(12) United States Patent
Kreber et al.

(10) Patent No.: US 9,662,430 B2
(45) Date of Patent: May 30, 2017

(54) DEVICE AND METHOD FOR CONVEYING A FLUID TO A FILTER UNIT OF A MEDICAL TREATMENT APPARATUS

(75) Inventors: Stefan Kreber, Saarbruecken (DE); Manfred Weis, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 663 days.

(21) Appl. No.: 13/446,247

(22) Filed: Apr. 13, 2012

(65) Prior Publication Data

US 2012/0261341 A1 Oct. 18, 2012

Related U.S. Application Data

(60) Provisional application No. 61/474,770, filed on Apr. 13, 2011.

(30) Foreign Application Priority Data

Apr. 13, 2011 (DE) .......................... 10 2011 016 869

(51) Int. Cl.
*A61M 1/16* (2006.01)
(52) U.S. Cl.
CPC ......... *A61M 1/1694* (2013.01); *A61M 1/1635* (2014.02); *A61M 2205/12* (2013.01); *A61M 2205/128* (2013.01)
(58) Field of Classification Search
CPC .................................................. A61M 1/1694
See application file for complete search history.

(56) References Cited

U.S. PATENT DOCUMENTS

| 3,669,880 A | | 6/1972 | Marantz et al. |
| 3,709,222 A | * | 1/1973 | DeVries .......................... 604/28 |
| 4,209,391 A | * | 6/1980 | Lipps et al. .................. 210/647 |
| 4,267,040 A | * | 5/1981 | Schal ............................ 210/104 |

(Continued)

FOREIGN PATENT DOCUMENTS

| DE | 81 17 448 U1 | 11/1981 |
| DE | 43 08 586 C1 | 5/1994 |

(Continued)

OTHER PUBLICATIONS

WO 2011-038858 Spec Machine Translation.*

(Continued)

*Primary Examiner* — Krishnan S Menon
*Assistant Examiner* — Bradley R Spies
(74) *Attorney, Agent, or Firm* — Kilyk & Bowersox, P.L.L.C.

(57) ABSTRACT

The invention relates to a device and a method for conveying a fluid to a filter unit of a medical treatment apparatus, in particular for conveying a dialysing fluid to a treatment unit, in particular a dialyser or filter of an extracorporeal blood treatment apparatus. The device comprises a balancing unit and a recirculation unit, which comprises one or more chambers. With the balancing unit, it is possible to supply fresh fluid continuously to the recirculation circuit and to discharge used fluid from the recirculation circuit. The supply and discharge of fresh and used dialysing fluid can take place at a flow rate other than the flow rate at which the fluid circulates in the recirculation circuit via the filter unit.

12 Claims, 7 Drawing Sheets

(56) References Cited

U.S. PATENT DOCUMENTS

| | | | |
|---|---|---|---|
| 5,119,676 A * | 6/1992 | Bower et al. | 73/290 V |
| 5,399,157 A | 3/1995 | Goux et al. | |
| 6,595,944 B2 * | 7/2003 | Balschat et al. | 604/6.09 |
| 2005/0131331 A1 * | 6/2005 | Kelly et al. | 604/4.01 |
| 2005/0131332 A1 * | 6/2005 | Kelly et al. | 604/4.01 |
| 2009/0008306 A1 * | 1/2009 | Cicchello et al. | 210/85 |
| 2009/0198170 A1 * | 8/2009 | Childers et al. | 604/6.09 |
| 2012/0223016 A1 * | 9/2012 | Weis | A61M 1/1635 |
| | | | 210/646 |

FOREIGN PATENT DOCUMENTS

| | | |
|---|---|---|
| DE | 10 2009 048 561 A1 | 4/2011 |
| WO | 2011/038858 A1 | 4/2011 |

OTHER PUBLICATIONS

DE8117448 Translated Spec.*
PCT International Search Report and Written Opinion from PCT/EP2012/001593, mailed on Jul. 4, 2012.
International Preliminary Report on Patentability (IPRP) dated Oct. 15, 2013 in PCT/EP2012/001593.

* cited by examiner

DEVICE AND METHOD FOR CONVEYING A FLUID TO A FILTER UNIT OF A MEDICAL TREATMENT APPARATUS

CROSS-REFERENCE TO RELATED APPLICATIONS

The present application claims priority to, and the benefit of, co-pending United States Provisional Application 61/474,770 filed on Apr. 13, 2011. The contents of this provisional application is incorporated herein by reference in its entirety. The present application also claims priority to, and the benefit of, German Patent Application DE 10 2011 016 869.9 filed on Apr. 13, 2011. The contents of this foreign application is incorporated herein by reference in its entirety.

FIELD OF THE INVENTION

The invention relates to a device and a method for conveying a fluid to a filter unit of a medical treatment apparatus, in particular for conveying a dialysing fluid to a treatment unit, in particular a dialyser or filter of an extracorporeal blood treatment apparatus. Moreover, the invention relates to an extracorporeal blood treatment apparatus which comprises a device for conveying dialysing fluid to a blood treatment unit, in particular a dialyser or filter.

BACKGROUND OF THE INVENTION

Various kinds of treatment apparatuses are known that comprise a treatment unit to be supplied with a fluid. The known treatment apparatuses include, for example, blood treatment apparatuses. During the blood treatment, the patient's blood flows in an extracorporeal blood circuit through the blood treatment unit. In the case of apparatuses for haemodialysis, haemofiltration and haemodiafiltration, the blood treatment unit is a dialyser or filter, which is divided by a semi-permeable membrane into a blood chamber and a dialysing fluid chamber.

During the dialysis treatment, the blood flows in an extracorporeal blood circuit through the blood chamber, whilst the dialysing fluid flows in a dialysing fluid circuit through the dialysing fluid chamber of the dialyser.

Considering the large exchange quantities, there is a need with the known methods and apparatuses for blood treatment for exact balancing of the fluid removed from the patient and the fluid fed to the patient during the overall treatment time. Gravimetric and volumetric balancing devices belong are known.

A haemodiafiltration apparatus with volumetric balancing is known for example from DE 26 34 238 A1. The balancing device of the known haemodiafiltration apparatus comprises a volume-rigid hollow body, which is divided by a mobile partition wall into two chambers. Each chamber comprises an inlet and an outlet, at which supply lines and discharge lines for fresh and, respectively, used dialysing fluid are disposed, a shut-off element being incorporated in each line. Moreover, provision is made for pumps for conveying the fresh and used dialysing fluid as well as for a control unit, which permits alternate filling of the two chambers.

In order to be able to ensure a continuous flow of dialysing fluid through the dialysing fluid chamber of the dialyser, two balancing chamber are connected in parallel in practice, said balancing chambers supplying the dialyser alternately with fresh dialysing fluid. A balancing unit with two balancing chambers is described in for example DE 28 38 414.

During a dialysis treatment, the dialysing fluid flow typically amounts to 500 ml/min, but can amount to up to 1000 ml/min depending on the given treatment situation. In the case of a dialysis period of 4 hours, this means a dialysing fluid requirement which typically amounts to approx. 120 1, but depending on the given treatment situation can also be over 200 1.

Because of the large fluid requirement in dialysis, the preparation of the dialysate from concentrates and pure water (RO water) in the machine has evolved, in order to avoid the storage of fairly large quantities of solutions. The RO water is made available centrally in the clinic and distributed via lines to the dialysis machines in the dialysis stations.

In the treatment of an acute renal insufficiency, such as can occur for example after accidents, which calls for intensive-care support for the patient, a RO water connection is generally not present. The dialysing fluid is then made available to the machine by means of containers, for example canisters or bags.

In order to keep the handling costs as low as possible, an attempt is made, especially in the case of intensive-care support for acute renal insufficiency, to reduce the requirement for dialysing fluid. This is achieved by the fact that the dialysing fluid is recirculated via the dialyser for a certain length of time. The dialysate requirement can thus be reduced to values which lie below 100 ml/min.

A blood treatment apparatus with a recirculation circuit is known for example from U.S. Pat. No. 5,685, 988. The recirculation of dialysing fluid should however only be used for the determination of blood treatment parameters.

The invention described herein provides a device for conveying fluids into the treatment unit of a medical treatment apparatus, in particular into the dialyser of a dialysis apparatus, with which device the requirement for dialysing fluid can be reduced and a recirculation of dialysing fluid is enabled. Further, the invention described herein provides a method for conveying fluids into the blood treatment unit of a medical treatment apparatus, said method permitting a reduction in the requirement for dialysing fluid and a recirculation of dialysing fluid. The invention described herein also provides an extracorporeal blood treatment apparatus with such a device for conveying fluids.

SUMMARY OF THE INVENTION

The device according to the invention and the method according to the invention are based on the fact that the fluid, in particular dialysing fluid, to be conveyed to the filter unit of the medical treatment apparatus, in particular the blood treatment unit of an extracorporeal blood treatment apparatus, circulates in a fluid circuit which includes the filter unit. In order to balance the fresh and used fluid which is respectively supplied to the filter unit and carried away from the filter unit, use is made of a balancing unit.

The device according to the invention comprises a recirculation unit which comprises one or more chambers. The recirculation unit is constituted such that a recirculation circuit including the filter unit is created, wherein fluid flows into the filter unit and out of the filter unit independently of the fluid flow into the balancing unit and out of the balancing unit.

With the balancing unit, it is possible to supply fresh fluid, in particular dialysing fluid, continuously to the recirculation circuit and to discharge used fluid, in particular dialysing fluid, from the recirculation circuit. The supply and discharge of the fresh and used dialysing fluid can take place at a flow rate other than the flow rate at which the fluid circulates in the recirculation circuit via the filter unit. The recirculation circuit permits, however, not only the adjustment of different flow rates, but also the maintenance of a continuous flow rate through the dialyser or filter, even when the fluid flow via the balancing unit is to be discontinuous. Fluid (ultrafiltrate) can be withdrawn from or supplied to the patient via the recirculation circuit including the filter unit independently of the supply and discharge of fresh and used dialysing fluid.

A discontinuous fluid flow via the balancing unit is present when the balancing unit comprises only one balancing chamber. A particularly simple structure of the balancing unit thus results. However, a discontinuous fluid flow is also possible with a balancing unit which comprises a plurality of balancing chambers. In this case, the fluid flow through the filter unit can be maintained by the recirculation circuit.

In a preferred embodiment, the recirculation unit comprises means for routing fluid out of the chambers of the recirculation unit into the filter unit and out of the filter unit into the chambers of the recirculation unit as well as a means for conveying fluid out of the chambers of the recirculation unit into the filter unit and out of the filter unit into the chambers of the recirculation unit.

The recirculation unit comprises a means for controlling the means for conveying fluid out of the chambers of the recirculation unit into the filter unit and out of the filter unit into the chambers, said means being constituted such that, alternately in successive operating steps, fluid is conveyed out of the filter unit into one of the chambers, while fluid is conveyed out of another of the chambers into the filter unit. A continuous fluid flow is thus maintained in the recirculation circuit. The fluid flows in the recirculation circuit at a rate which results from the step frequency and the filling volume with which the chambers of the recirculation unit are operated. In a particularly preferred embodiment, the recirculation unit comprises a first and second chamber, which are alternately filled with fluid or emptied.

A further preferred embodiment of the balancing unit, which comprises a first and a second chamber, provides a means for routing fresh fluid from a fluid source into the chambers of the balancing unit and for routing used fluid out of the chambers into a drain and for routing fresh fluid out of the chambers into the filter unit and used fluid out of the filter unit into the chambers as well as a means for conveying fluid in the means for routing fluid.

Moreover, the balancing unit comprises a means for controlling the means for conveying fluid, which are constituted such that, in successive operating steps, the first and second chamber of the balancing unit are alternately filled with fresh and used dialysing fluid. Each chamber of the two chambers of the balancing unit is filled both with fresh fluid as well as used fluid, wherein the functions of the chambers are alternately exchanged. Exact balancing can thus be achieved even when the volumes of the two chambers differ from one another. Over the whole treatment period, divergences in the volumes of the chambers are mutually compensated for on account of the cyclical exchange. It is advantageous especially when the control of the chambers takes place as a function of the filling level of the chambers. This is because, when there are differing volumes of the chambers, it is not possible from the filling level alone to draw conclusions about the fluid quantity contained in the chambers.

The means for controlling the means for conveying fluid of the balancing unit are preferably constituted such that, in a preceding operating step of successive operating steps, fresh fluid is conveyed out of the first chamber into the filter unit, while used fluid is conveyed out of the filter unit into the second chamber. In a subsequent operating step, fresh fluid from the fluid source is conveyed out of the second chamber into the filter unit, while used fluid is conveyed out of the filter unit into the first chamber. Consequently, both chambers are alternately filled both with fresh and used fluid, in particular with fresh or used dialysing fluid.

It is not important for the invention how the fluid gets into or out of the chambers of the circulation unit and balancing unit. The means for conveying fluid assigned to the recirculation unit and the balancing unit preferably comprise a means for subjecting the chambers of the recirculation unit and the balancing unit to an overpressure and/or an underpressure and a means for opening and shutting off the means for routing fluid, which are assigned to the recirculation unit and the balancing unit. The means for routing fluid are preferably hose lines or flow paths integrated into a hard part, in which the fluid flows. The means for opening and shutting-off can be conventional shut-off elements, for example electromagnetically or pneumatically operated valves.

A particularly preferred embodiment of the invention provides that both the recirculation unit and the balancing unit each comprise a first and a second chamber. In total, therefore, there are four chambers, which can be made available in an article (disposable) intended for one-off use, as a result of which equipping of the medical treatment apparatus, in particular the extracorporeal blood treatment apparatus, with permanently installed chambers becomes unnecessary. The costly sterilisation of the chambers is therefore also unnecessary. Chambers constituted as a disposable, which are filled with fresh or used dialysing fluid are known, for example from DE 198 30 928 C1 and DE 195 46 028 C2.

With a disposable according to the invention having four chambers, two chambers form the recirculation unit and two chambers form the balancing unit. Whereas the two chambers of the balancing unit are preferably operated in such a way that the chambers are alternately filled both with fresh and used dialysing fluid, in order to achieve exact balancing even when the volumes of the two chambers differ from one another, the fluid flow through the filter unit, in particular the treatment unit of the extracorporeal blood treatment apparatus, is maintained with the recirculation unit even when the fluid flow is not continuous on account of the cyclical exchange of the chambers of the balancing unit. Thus, when fluid cannot be made available with the balancing unit in individual operating steps during the balancing, for example on account of the filling or emptying of the two chambers of the filter unit, the recirculation unit maintains the fluid flow through the filter unit.

Moreover, the device according to the invention permits the adjustment of a relatively high delivery rate through the filter unit, in particular a relatively high dialysing fluid rate, which can lie for example at 300 ml/min, with a relatively low intake of fresh fluid, in particular dialysing fluid. The intake of fresh dialysing fluid can be only a fraction of the intake of dialysing fluid that is flowing into the treatment unit, for example 50 ml/min. The consumption of fresh dialysing fluid is thus minimised, but the dialysate flow through the filter is nonetheless kept high. This is particularly advantageous in the case of mobile haemodialysis machines and dialysis machines for acute dialysis treatment, since the dialysing fluid in the case of such machines is made available in bags or canisters.

Moreover, the device according to the invention can also be used in an advantageous way with dialysis apparatuses which comprise a dialysing fluid circuit that comprises a first and a second dialyser or filter in order to enable efficient removal of medium-sized molecules with a relatively small blood flow. Such a dialysis apparatus is for example described in DE 10 2009 026 901 A1.

An example of embodiment of the invention is explained in greater detail below by reference to the drawings.

DETAILED DESCRIPTION OF THE INVENTION

Figure 1:
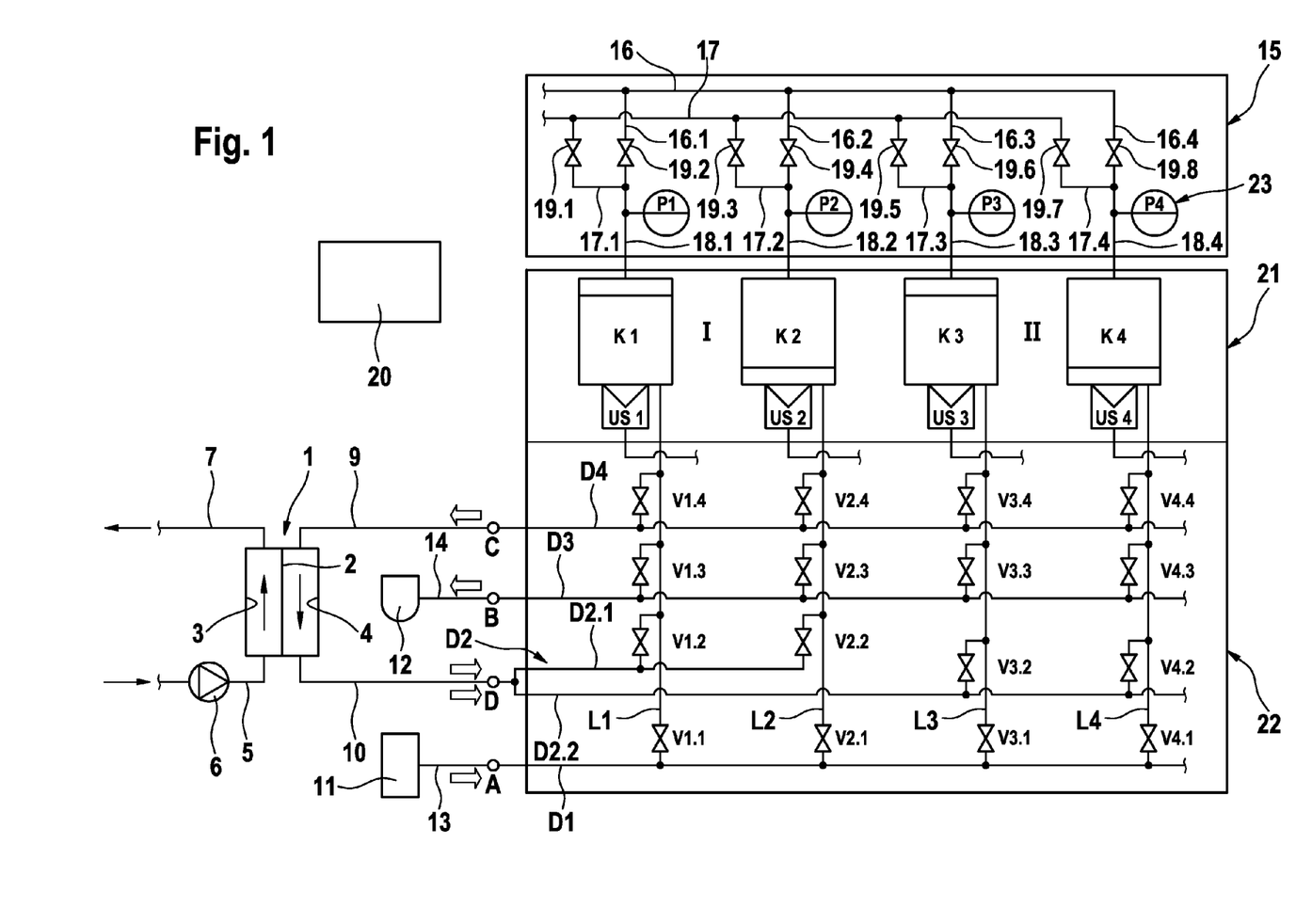
FIG. 1 shows a very simplified schematic representation of a medical treatment apparatus, in particular a dialysis apparatus, which comprises a device for conveying a fluid to a filter unit of the medical treatment apparatus, in particular to the treatment unit of an extracorporeal blood treatment apparatus.

FIG. 1 shows a very simplified representation of the device according to the invention for conveying a fluid to a filter unit of a medical treatment apparatus. In the present example of embodiment, the device according to the invention is used to supply an extracorporeal blood treatment apparatus, in particular a dialysis apparatus, with fresh dialysing fluid, which is made available in a dialysing fluid source, in particular a bag. The device for conveying dialysing fluid is referred to below is a supply device.

The supply device can form an independent unit or be a component part of the dialysis apparatus. The device according to the invention is preferably a component part of the dialysis apparatus. The medical treatment apparatus, in particular the dialysis apparatus, is therefore described below together with the device for conveying a fluid, in particular a dialysing fluid, to the filter unit, in particular the dialyser, of the extracorporeal blood treatment apparatus.

The medical treatment apparatus, in particular the dialysis apparatus, comprises a dialyser 1 as a filter unit, which is divided by a semipermeable membrane 2 into a blood chamber 3 and a dialysing fluid chamber 4. Connected to the inlet of blood chamber 3 of dialyser 1 is a blood supply line 5, into which a blood pump 6 is incorporated. Leading away from the outlet of blood chamber 3 of dialyser 1 is a blood discharge line 7, which leads to the patient. A dialysing fluid supply line 9 leads to the inlet of dialysing fluid chamber 4 and a dialysing fluid discharge line 10 leads away from the outlet of dialysing fluid chamber 4. Fresh dialysing fluid is supplied to the dialyser via the dialysing fluid supply line, while used dialysing fluid is carried away via dialysing fluid discharge line 10.

Fresh dialysing fluid is made available in a dialysing fluid source 11, in particular a bag or a canister. Used dialysing fluid is discharged into a drain 12, which can also be a bag or canister. Dialysing fluid bag 11 is connected via a supply line 13 for fresh dialysing fluid to an intake A of the supply device. Drain 12 is connected via a drain-off line 14 for used dialysing fluid to a drain B of the supply device. Dialysing fluid supply line 9 is connected to a drain C and dialysing fluid discharge line 10 is connected to an intake D of the supply device. Consequently, fresh dialysing fluid is supplied via dialysing fluid supply line 9 of dialysing fluid chamber 4 and used dialysing fluid is discharged via dialysing fluid discharge line 10. Fresh dialysing fluid is thus balanced against used dialysing fluid.

In the present example of embodiment, fresh dialysing fluid is fed by means of the supply device to single dialyser 1 of the dialysis apparatus. The dialysis apparatus can however also comprise two filters, as is described for example in DE 10 2009 026 901 A1. Fresh dialysing fluid is then supplied by means of the supply device to the first filter.

The supply device comprises a balancing unit I for balancing fresh dialysing fluid against used dialysing fluid. Moreover, the supply device comprises a recirculation unit II for recirculating dialysing fluid through dialysing fluid chamber 4 of dialyser 1, while fresh dialysing fluid is supplied and used dialysing fluid is discharged.

Balancing unit I comprises a first fluid chamber K1 and a second fluid chamber K2. Recirculation unit II also comprises a first fluid chamber K3 and a second fluid chamber K4. The supply device thus comprises a total of four fluid chambers K1-K4. All the fluid chambers are a component part of an article (disposable) intended for one-off use.

The disposable is inserted into a suitable receiving unit 21 of the dialysis apparatus, which is represented merely by way of indication in FIG. 1.

The supply device comprises, apart from chambers K1-K4, means for routing and means for conveying fresh and used dialysing fluid from dialysing bag 11 to chambers K1 and K2 of balancing unit I and from chambers K1 and K2 of the balancing unit to drain 12 as well as from chambers K3 and K4 of recirculation unit II to dialysing fluid chamber 4 and from dialysing fluid chamber 4 to chambers K3 and K4 of recirculation unit II. These means comprise hose lines or flow paths in a hard part, which are a component part of disposable 21, and a device 15, a means for conveying fluid, for subjecting chambers K1-K4 of balancing unit I and recirculation unit II to an overpressure and/or an underpressure, said device being referred to below as pneumatic device 15. The arrangement of device 15 together with chambers K1-K4 provides for a means for pumping fluid. Thus the device 15 therein provides a means for building up an overpressure and/or underpressure.

Pneumatic device 15 comprises a pressure line 16, from which spur lines 16.1, 16.2, 16.3, 16.4 branch off, which lead to chambers K1, K2, K3, K4 of balancing unit I and a recirculation unit II, in order to build up an overpressure in the individual chambers. Moreover, pneumatic device 15 comprises a pressure line 17, from which spur lines 17.1, 17.2, 17.3, 17.4 branch off, which also lead to chambers K1, K2, K3, K4, in order to build up an underpressure in the individual chambers. The spur lines leading away from first and second pressure line 16, 17 are in each case brought together to a common line segment 18.1, 18.2, 18.3, 18.4 which is connected to chambers K1, K2, K3, K4. An overpressure is present on pressure line 16 and an underpressure is present on pressure line 17. A shut-off element 19.1, 19.2, 19.3, 19.4, 19.5, 19.6, 19.7, 19.8 is incorporated in each case into the individual spur lines. By opening and closing shut-off elements 19.1-19.8, chambers K1-K4 can thus be subjected to overpressure or underpressure, whereby pressure lines 16 and 17, line segments 18.1-18.4, and shut-off elements 19.1-19.8 provide a means for building up an overpressure and/or underpressure in a chamber. The shut-off elements are preferably pneumatically or electromagnetically operated valves. Ventilation valves can also be provided, which however are not represented in FIG. 1.

The control of the shut-off elements takes place with a central control and computing unit 20, which is a component part of the dialysis apparatus. Shut-off elements 19.1-19.8 of pneumatic device 15 are connected by control lines (not represented) to central control and computing unit 20. Control and computing unit 20, a controlling means, also controls blood pump 6 and all the other units of the dialysis apparatus.

The supply device further comprises an arrangement of lines and shut-off elements which are a component part of disposable 21, in order to connect in each case one of chambers K1-K4 to one of intakes or drains A-D. This arrangement is constituted in the manner of a "matrix", which comprises four "rows" and four "columns".

A line D1, D2, D3, D4 ("rows") is connected to each intake or drain A, B, C, D, while a means for routing fluid such as a line L1, L2, L3, L4 ("columns"), is connected to each chamber K1, K2, K3, K4. Common line segments 18.1-18.4 of pressure lines 16, 17 are connected to one side of the chambers and the connections of fluid lines L1, L2, L3, L4 to the other side of the chambers, so that the connections lie opposite one another. Each line D1-D4, a means for routing fluid, is connected to each line L1-L4 via a shut-off element (valve) V 1.1-V 4.4. The shut-off elements are disposed in rows and columns. The arrangement of the valves in the manner of a "matrix" is denoted below as valve arrangement 22, which functions as a means for creating a flow connector. The shut-off elements of valve arrangement 22 are also preferably pneumatically or electromagnetically operated valves.

Furthermore, the supply device comprises means US1, US2, US3, US4 for detecting the filling level of chambers K1, K2, K3, K4, which are represented solely by way of indication.

The means for detecting the filling level of the chambers are connected to central control and computing unit 20.

The means for detecting the filling level are preferably ultrasonic sensors US1, US2, US3, US4, which detect the height of the filling level of the chambers on the basis of a measurement of transit time. Each chamber K1, K2, K3, K4 has an ultrasonic filling level sensor US1, US2, US3, US4 assigned to it. The ultrasonic filling level sensors each have an ultrasonic emitter and an ultrasonic receiver which are preferably formed by one component which can act as an emitter and receiver. The ultrasonic emitter/receiver may for example be a piezoelectric component. Otherwise, the ultrasonic emitter and ultrasonic receiver of an ultrasonic filling level sensor are preferably arranged in a single plane.

The ultrasonic filling level sensors are so disposed on or in the chambers that ultrasonic pulses are coupled into the fluid, are reflected at the interface between the fluid and the air, and are coupled out again from the fluid. The interface between the fluid and the air represents the filling level in this case. The ultrasonic sensors are preferably disposed on the floors of the chambers, in which case the sensors may be situated inside or outside the chambers.

The individual ultrasonic filling level sensors US1, US2, US3, US4 have assigned to them a measuring unit (not shown in the drawings) which calculates the filling level in each of the chambers K1, K2, K3, K4 on the basis of a measurement of transit time. The measuring unit is programmed in such a way that the distance covered by the pulses in the fluid, which is equal to twice the height of the filling level, is calculated from the transit time of the pulses in the fluid and their speed of propagation therein. The speed of propagation can be assumed to be the speed of sound in this case. The measuring unit is preferably programmed in such a way that, when the ultrasonic pulses are being analysed, allowance is made for the density and temperature of the medium. The density of the medium on which measurements are being made may for example be stored in a memory of the measuring unit or may be entered in the memory by the user. The measuring unit may be calibrated to a given temperature and density for the fluid.

The individual operating steps, in which fluid flows into chambers K1-K4 and out of chambers K1-K4, are described below.

The operating steps of recirculation unit II are first described, with which a flow of dialysing fluid is maintained through dialysing fluid chamber 4 of dialyser 1.

Figure 2A:
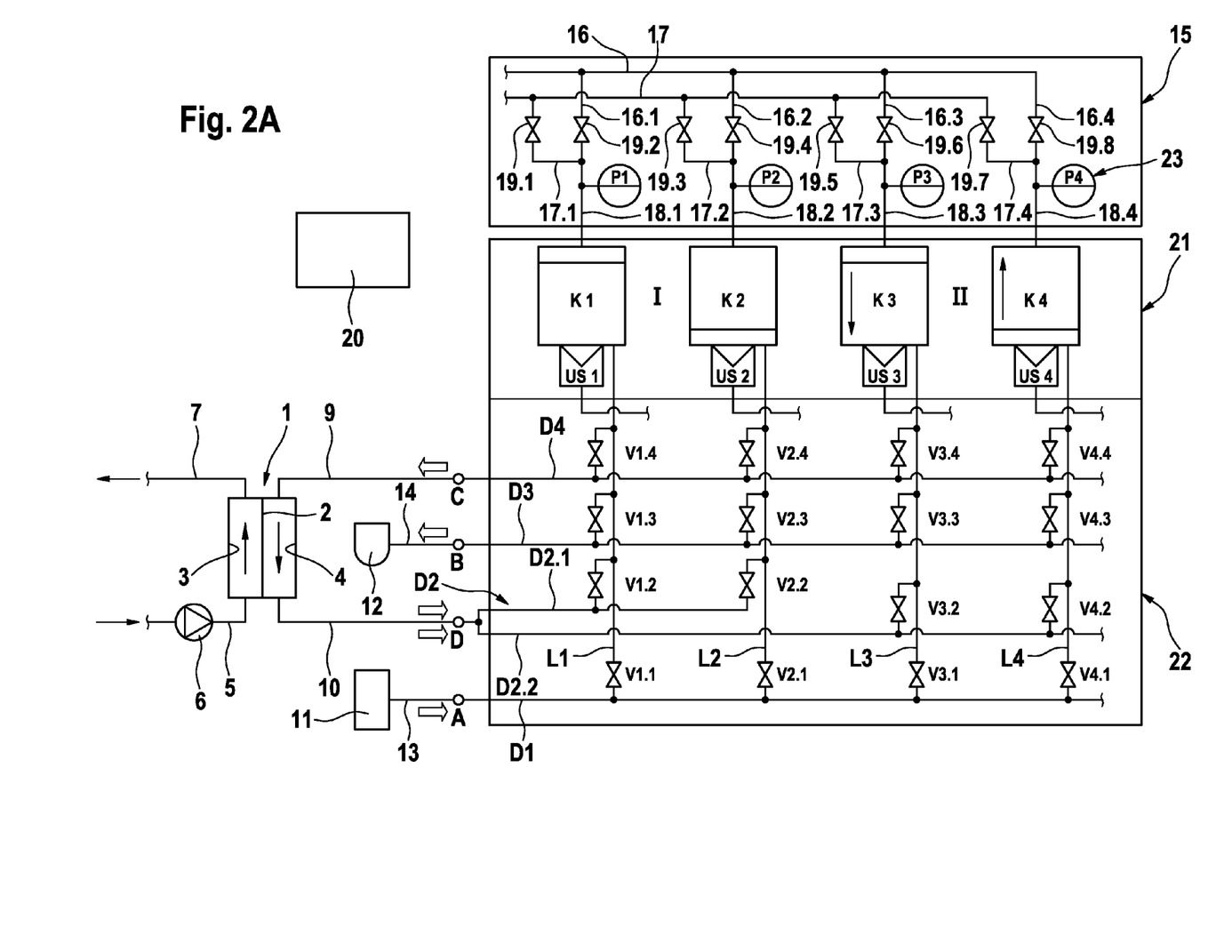
FIG. 2A-2B show the individual operating steps of the recirculation unit of the device according to the invention and FIG. 3A-3D show the individual operating steps of the balancing unit of the device according to the invention.
Figure 2B:
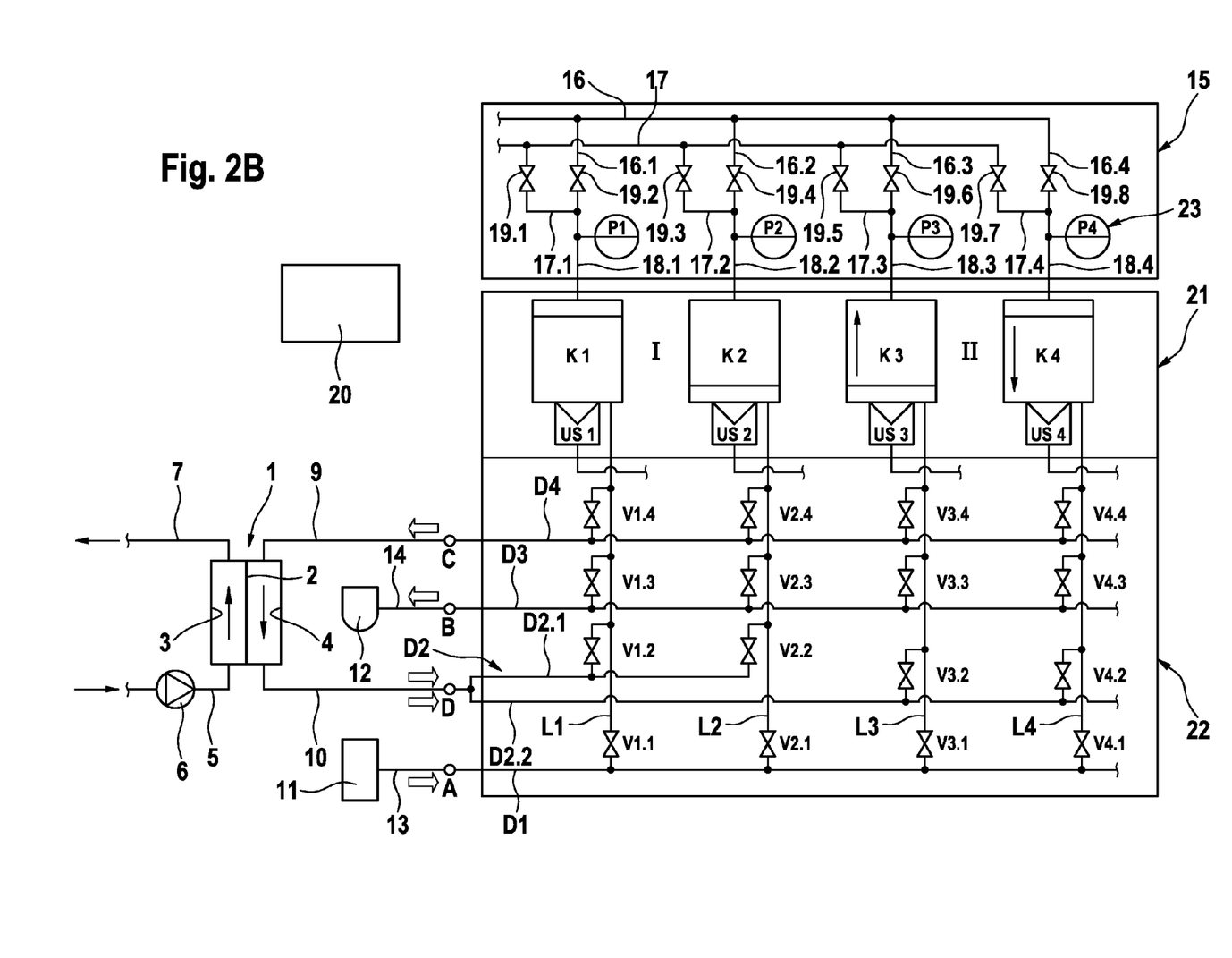

FIGS. 2A and 2B illustrate the successive operating steps of successive operating cycles, in which dialysing fluid flows into and respectively out of chambers K3 and K4 of recirculation unit II. Shut-off elements V 1.1-V 4.4, which are opened by control and computing unit 20, are indicated in FIGS. 2A and 2B.

FIG. 2A shows the first operating step of an operating cycle. In the first operating step, fresh dialysing fluid flows out of chamber K3 into dialysing fluid chamber 4, while used dialysing fluid flows out of dialysing fluid chamber 4 of dialyser 1 into chamber K4 of recirculation unit II. For this purpose, control and computing unit 20 opens valves V3.4 and V4.2 of valve arrangement 22 and valves 19.6 and 19.7 of pneumatic device 15, while the other valves are closed. Consequently, chamber K3 is subjected to an overpressure and chamber K4 to an underpressure, so that dialysing fluid flows via lines L3, D4, D2.2, L4 out of chamber K3 through dialysing fluid chamber 4 of dialyser 1 into chamber K4. The flow direction is marked by arrows in FIG. 2A. The fluid flow is reversed in the second operating step of the same operating cycle. The control and computing unit now opens valves V4.4 and V3.2 of valve arrangement 22 and valves 19.8 and 19.5 of pneumatic device 15, so that dialysing fluid flows out of chamber K4 through dialysing fluid chamber 4 into chamber K3 of balancing unit I.

The operating cycle described above is again followed by the same operating cycle with two operating steps.

Whereas dialysing fluid is conveyed continuously with recirculation unit II through dialyser 1, fresh dialysing fluid is balanced against used dialysing fluid with balancing unit I, wherein fresh dialysing fluid is supplied from dialysing fluid source 11 and used dialysing fluid flows away into drain 12. The individual operating steps of this operating cycle are described below by reference to FIGS. 3A-3E. The double arrows in K3 and K4 of FIGS. 3A-3E symbolise the continuous recirculation of dialysing fluid during the balancing process.

Figure 3A:
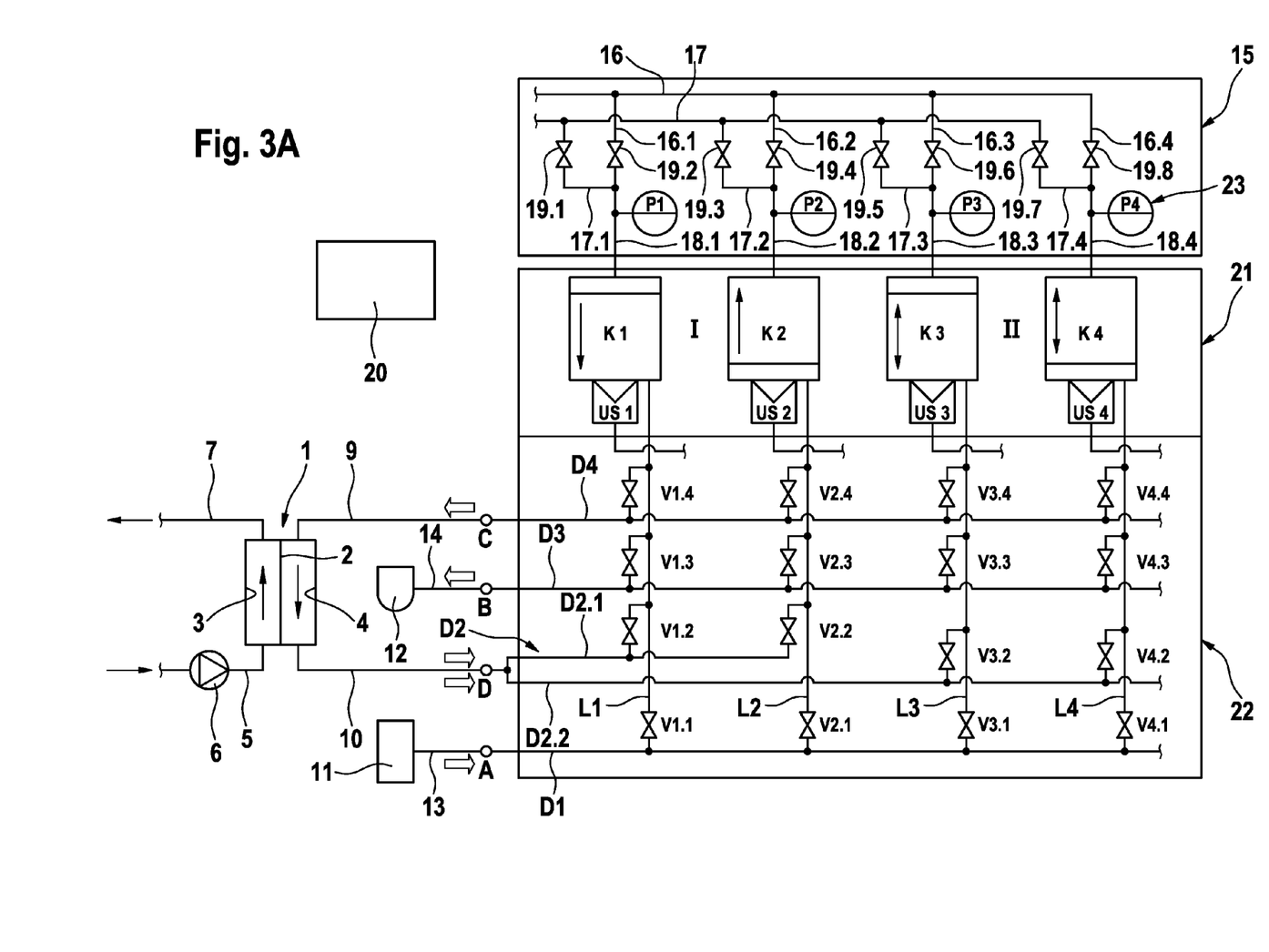

It is assumed that chamber K1 is filled with fresh dialysing fluid and chamber K2 is empty in the first operating step of an operating cycle. In the first operating step, valves V1.4 and V2.2 of valve arrangement 22 and valves 19.2 and 19.3 of pneumatic device 15 are opened by control and computing unit 20, the other valves being closed. Chamber K1 is thus subjected to overpressure and chamber K2 of balancing unit I to underpressure. Fresh dialysing fluid thus flows out of chamber K1 via lines L1, D4, D2.1, L2 through dialysing fluid chamber 4 of dialyser 1 and displaces used dialysing fluid out of dialysing fluid chamber 4 into chamber K2 (FIG. 3A).

Figure 3B:
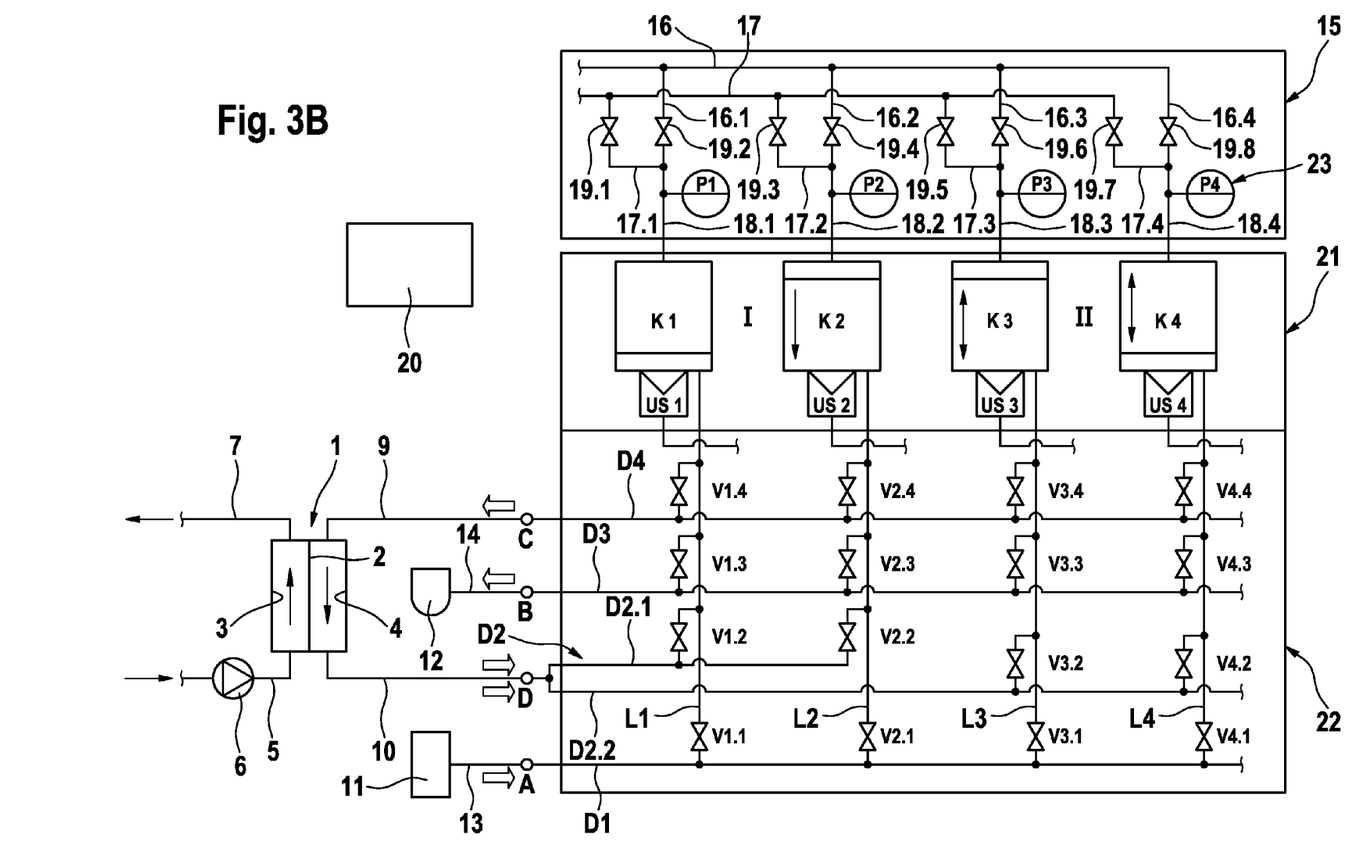

In the second operating step, the used dialysing fluid is discarded from chamber K2. For this purpose, valve V2.3 of valve arrangement 21 and valve 19.4 of pneumatic device 15 are opened, while the other valves are closed. Since chamber K2 is subjected to an overpressure, the used dialysing fluid flows into drain 12 (FIG. 3B).

Figure 3C:
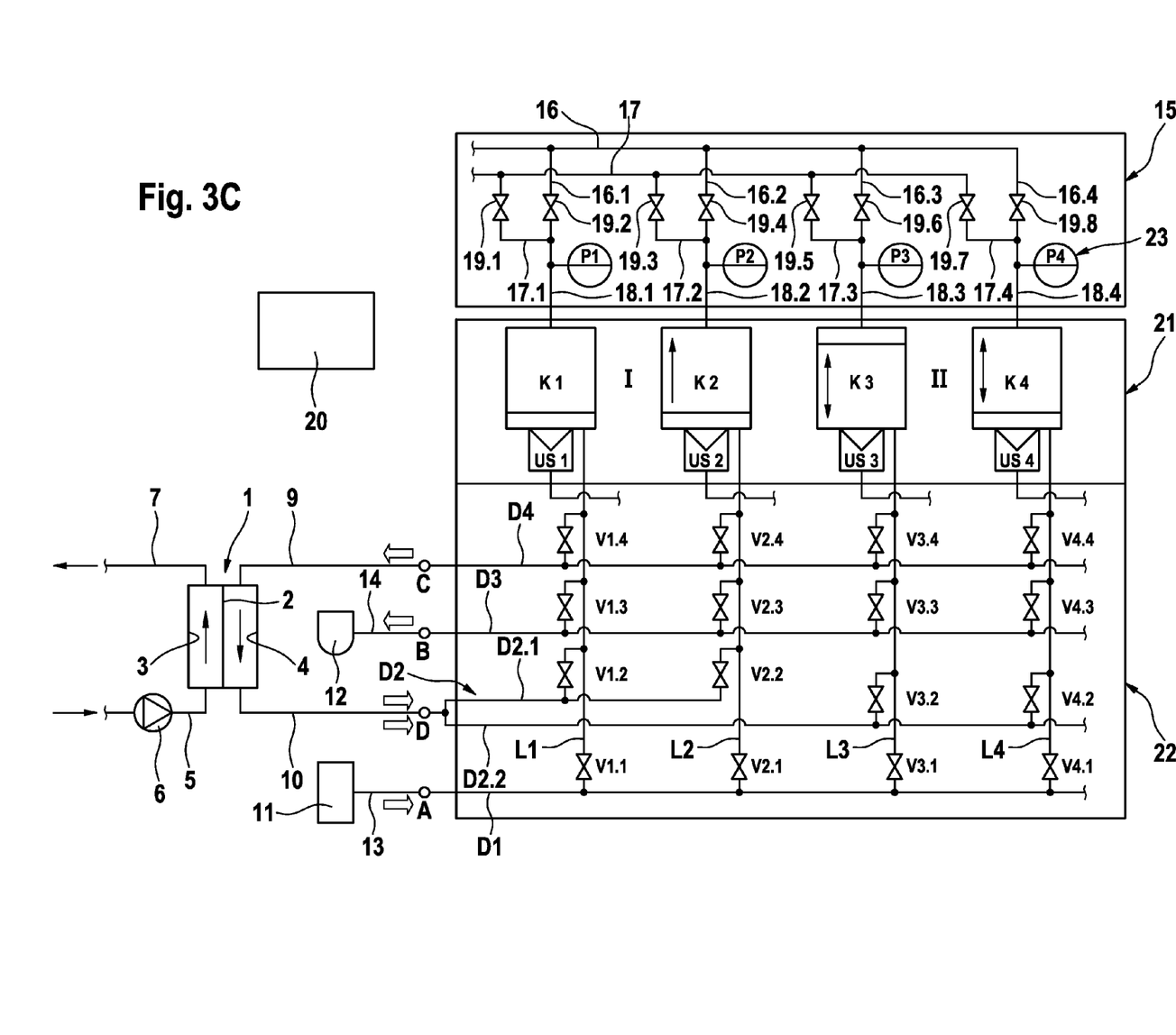
Figure 3D:
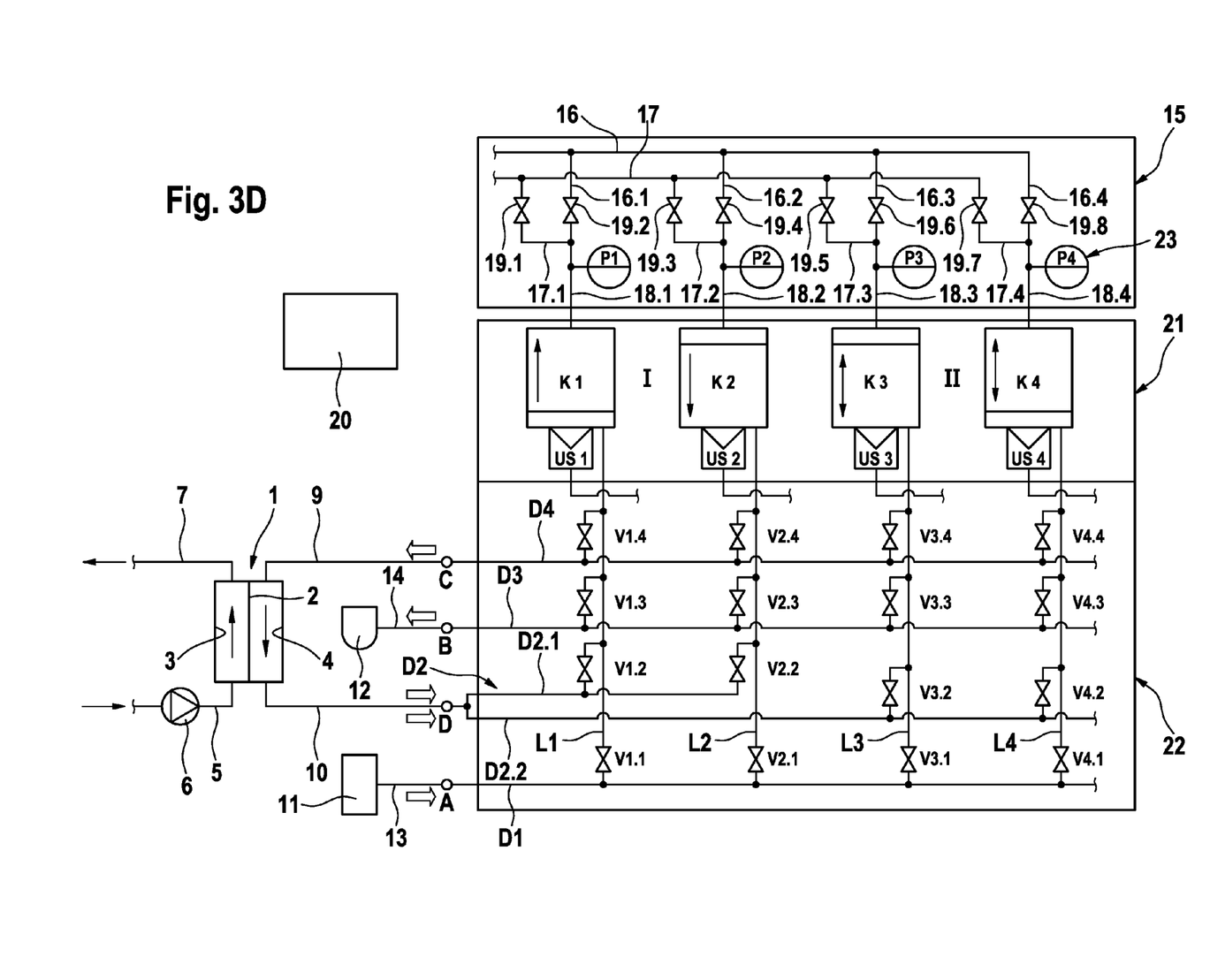

A third operating step follows, in which chamber K2 is filled with fresh dialysing fluid from dialysing fluid source 11. For this purpose, valve V2.1 of valve arrangement 22 and valve 19.3 of pneumatic device 15 are opened, while the other valves are closed, so that fresh dialysing fluid is sucked into chamber K2 (FIG. 3C).

The fourth operating step now follows, in which the fresh dialysing fluid from chamber K2 displaces used dialysing fluid into chamber K1 via dialyser 1. For this purpose, valves V2.4 and V1.2 of valve arrangement 22 and valves 19.4 and 19.1 of pneumatic device 15 are opened, while the other valves are closed, so that an overpressure is built up in chamber K2 and an underpressure in chamber K1. The operating steps described above form an operating cycle, which is followed again by an operating cycle which comprises the operating steps described above (FIG. 3D).

Chambers K1 and K2 of balancing unit I thus remove fresh dialysing fluid from dialysing fluid bag 11 in order to supply the dialysing fluid to the dialysing fluid circuit. Fresh dialysing fluid is thereby balanced against used dialysing fluid, wherein fluid can be withdrawn from (ultrafiltration) or fluid can be supplied to the fluid system. The supply or the withdrawal of fluid can take place by the fact that more or less fluid is supplied to or withdrawn from the one or other chamber. Instead of a differing filling of the chambers with dialysing fluid, it is also possible in one or more operating steps to withdraw only used dialysing fluid from the fluid system or to supply only fresh dialysing fluid to the fluid system, in order to supply fluid to the system or to withdraw it therefrom.

Control and computing unit 20 controls the switch-over of individual valves V1.1. to V4.1 depending on the filling level of the chambers. Since the chambers and the associated lines can have differing volumes, it is not ensured solely by detecting the filling level that equal quantities of fresh dialysing fluid are balanced against used dialysing fluid. This possible error is avoided by the fact that both chambers are each filled with fresh and with used dialysing fluid and are cyclically interchanged. Possible errors are thus compensated for over the individual operating cycles.

In the present example of an embodiment, the individual chambers can be subjected both to an overpressure and to an underpressure in order to convey dialysing fluid from the one into the other chamber. In principle, however, it is also possible to subject only the one or the other of the two chambers to an overpressure or underpressure.

Since the balancing unit comprises only two chambers, individual operating steps in which dialysing fluid does not flow through the dialyser arise with the alternating filling of the chambers with fresh and used dialysing fluid. Consequently, the fluid flow through the dialyser is discontinuous. However, this is not disadvantageous, since the fluid flow through the recirculation unit is in any case maintained. Moreover, it is possible with the recirculation unit to set higher flow rates than the flow rate at which fresh dialysing fluid is supplied or used dialysing fluid discharged. A relatively small consumption of dialysing fluid thus results even with a high flow rate through the dialyser. This is advantageous especially in the case of dialysis apparatuses for acute dialysis.

The operation of balancing unit I and of recirculation unit II permits the simple measurement of the pressure both in lines L, D of the fluid system of the supply device as well as in lines 9, 10, 13, 14 of the fluid system of the extracorporeal blood treatment apparatus, which are connected to lines L, D of the fluid system of the supply device.

In order to measure the pressure, the supply device comprises a pressure measuring device 23, which comprises means for measuring the pressure. The means for measuring the pressure are pressure sensors P1, P2, P3, P4, which are connected to common line segments 18.1, 18.2, 18.3, 18.4 of pressure lines 16, 17, so that the pressure sensors detect the pressure in individual chambers K1, K2, K3, K4. In the present example of embodiment, pressure sensors P1-P4 are not a component part of the disposable, but are disposed on the machine side. Pressure measuring device 23 is connected via a data line (not shown) to central computing and control unit 20 of the blood treatment apparatus. The pressure measurement values for the control of the blood treatment are evaluated in the central computing and control unit.

During the operation of balancing unit and recirculation unit I, II described by reference to FIGS. 2 and 3, shut-off elements V1.1-V4.4 are opened or closed, so that fresh dialysing fluid is balanced against used dialysing fluid and dialysing fluid flows through balancing chamber 2 of dialyser 1. When individual shut-off elements are opened, a flow connection is produced between lines L1, L2, L3, L4 and lines D1, D2, D3, D4. Consequently, the pressure in lines D1, D2, D3, D4 can be measured with pressure sensor Pl, P2, P3, P4 that detects the pressure in the chamber which is connected to respective line L1, L2, L3, L4. For example, pressure sensor P1 measures the pressure in line D4 and line 9 when shut-off element V1.4 is opened, but all the other shut-off elements are closed. The pressure in all the lines can thus be measured by opening and closing the respective shut-off elements.

In the present example of an embodiment, pressure measuring device 23 comprises four pressure sensors P1-P4. It is thus possible to measure the pressure in a plurality of lines simultaneously. It is however also possible for the pressure measuring device to comprise only one, two or three pressure sensors. Even when the pressure measuring device comprises only one pressure sensor, for example only pressure sensor P1, the pressure in all the lines can be measured with the single pressure sensor. In this case, the pressure measurement in all the lines can however only take place one after the other. Simultaneous measurement of the pressure at all four points of the fluid system requires the four pressure sensors P1-P4.

Pressure sensors P1-P4 can measure the pressure in the chambers continuously, the measured values being read out only at specific times. These time points are a result of the step sequence in the operation of the chambers.

Valve arrangement 22 also permits an initial functional test of individual pressure sensors P1-P4, wherein the pressure sensors are connected to one another by opening or closing respective shut-off elements V1.1-V4.4. A functional test of the pressure sensors as well as a calibration of the sensors is thus possible, since the measurement of the pressure with all the sensors must lead to the same measurement result.

The invention claimed is:

1. A method of conveying fluids to a filter unit of a medical treatment apparatus, the medical treatment apparatus comprising a device including a recirculation unit and a balancing unit, the recirculation unit comprising first and second recirculation chambers and the balancing unit comprising first and second balancing chambers, wherein fresh fluid is balanced against used fluid in the balancing unit, the method comprising:

continuously conveying, via the recirculation unit, (1) fresh fluid out of the first recirculation chamber and into and through the filter unit to form used fluid, (2) the used fluid out of the filter unit and into the second recirculation chamber, and (3) the used fluid out of the second recirculation chamber, into the filter unit, out of the filter unit, and into the first recirculation chamber, wherein the fresh fluid and the used fluid are conveyed through the filter unit in a same direction and independently of fluid flow through the balancing unit; and conveying, via the balancing unit, (1) fresh fluid out of the first balancing chamber and into and through the filter unit to form used fluid, and (2) the used fluid out of the filter unit and into the second balancing chamber, wherein a fluid flow rate of the used fluid flowing out of the filter unit is independent of a fluid flow rate of the used fluid flowing into the balancing unit and the fluid flow rate of the fresh fluid flowing out of the balancing unit, and wherein the device is configured to maintain a continuous flow rate of fluid through the filter unit if the fluid flow rate of the fresh fluid flowing out of the balancing unit is discontinuous.

2. The method according to claim 1, wherein, alternately in successive operating steps, fluid is conveyed out of the filter unit and into one of the first and second recirculation chambers, while fluid is conveyed out of another of the first and second recirculation chambers and into the filter unit.

3. The method according to claim 2, wherein, alternately in successive operating steps, fluid is conveyed out of the filter unit and into one of the first and second recirculation chambers, while fluid is conveyed out of the other of the first and second recirculation chambers and into the filter unit.

4. The method according to claim 2, wherein, in a preceding operating step of successive operating steps, fresh fluid is conveyed out of the first recirculation chamber and into the filter unit, while used fluid is conveyed out of the filter unit and into the second recirculation chamber, and, in a subsequent operating step, fresh fluid from a fluid source is conveyed out of the second recirculation chamber into the filter unit, while used fluid is conveyed out of the filter unit into the first recirculation chamber, so that both the first and second recirculation chambers are filled alternately with fresh and used fluid.

5. The method according to claim 1, wherein an overpressure or under pressure is produced in the first and second recirculation chambers or the first and second balancing chambers in order to convey fluid.

6. The method according to claim 1, wherein the filter unit is a blood treatment unit.

7. The method according to claim 6, wherein the blood treatment unit is a dialyser or a dialysate filter.

8. The method according to claim 1, wherein the fluid is a dialysing fluid.

9. The method according to claim 1, wherein, to change over the first and second recirculation chambers and the first and second balancing chambers, the filling level in the first and second recirculation chambers and the first and second balancing chambers is determined on the basis of the transit time of ultrasonic pulses which enter the fluid situated in the first and second recirculation chambers and the first and second balancing chambers, are reflected at an interface between the fluid and air in the respective chamber, and leave the fluid.

10. A device for conveying a fluid to a filter unit of a medical treatment apparatus, the device comprising:

a balancing unit in fluid communication with the filter unit, the balancing unit comprising a first balancing chamber and a second balancing chamber, the balancing unit configured to balance a fresh fluid against a used fluid, a recirculation unit in continuous fluid communication with the filter unit independent of the fluid communication between the balancing unit and the filter unit, the recirculation unit comprising a first recirculation chamber and a second recirculation chamber, each chamber of the recirculation unit and the balancing unit having at least one ultrasonic filling level sensor, the ultrasonic filling level sensors each having an ultrasonic emitter and an ultrasonic receiver, the ultrasonic filling level sensors being so disposed on or in the chambers that the ultrasonic pulses emitted by a respective one of the ultrasonic emitters enter fluid situated in the respective chamber, are reflected at an interface between the fluid and air in the respective chamber, leave the fluid, and are received by the respective ultrasonic receiver, a filling level measuring unit configured to receive measurements from the ultrasonic filling level sensors, and calculate the filling level in the respective chambers on the basis of the measurements from the ultrasonic filling level sensors, wherein the filling level measuring unit is calibrated for a given temperature and density of the fluid, and a control and computing unit, wherein the control and computing unit is programmed such that:
  (a) the recirculation unit (1) conveys a fresh fluid out of the first recirculation chamber and into and through the filter unit to form a used fluid and conveys the used fluid out of the filter unit and into the second recirculation chamber, (2) conveys the used fluid out of the second recirculation chamber, into the filter unit, out of the filter unit, and into the first recirculation chamber, and (3) conveys the fresh fluid and the used fluid through the filter unit in a same direction,
  (b) a fluid flow rate of the used fluid flowing out of the filter unit is independent of a fluid flow rate of the used fluid flowing into the balancing unit and is independent of a fluid flow rate of the fresh fluid flowing out of the balancing unit, and
  (c) a continuous flow rate of fluid through the filter unit is maintained if the fluid flow rate of the fresh fluid flowing out of the balancing unit is discontinuous.

11. A device for conveying a fluid to a filter unit of a medical treatment apparatus, the device comprising:

a balancing unit in fluid communication with the filter unit, the balancing unit comprising a first balancing chamber and a second balancing chamber, the balancing unit configured to balance a fresh fluid against a used fluid, a recirculation unit in continuous fluid communication with the filter unit independent of the fluid communication between the balancing unit and the filter unit, the recirculation unit comprising a first recirculation chamber and a second recirculation chamber, each chamber of the recirculation unit and the balancing unit having at least one ultrasonic filling level sensor, the ultrasonic filling level sensors each having an ultrasonic emitter and an ultrasonic receiver, the ultrasonic filling level sensors being so disposed on or in the chambers that the ultrasonic pulses emitted by a respective one of the ultrasonic emitters enter fluid situated in the respective chamber, are reflected at an interface between the fluid and air in the respective chamber, leave the fluid, and are received by the respective ultrasonic receiver, and a control and computing unit, wherein the control and computing unit is programmed such that:

(a) the recirculation unit (1) conveys a fresh fluid out of the first recirculation chamber into and through the filter unit to form a used fluid and conveys the used fluid out of the filter unit and into the second recirculation chamber,(2) conveys the used fluid out of the second recirculation chamber, into the filter unit, out of the filter unit, and into the first recirculation chamber, and (3) conveys the fresh fluid and the used fluid through the filter unit in a same direction, (b) a fluid flow rate of the used fluid flowing out of the filter unit is independent of a fluid flow rate of the used fluid flowing into the balancing unit and is independent of a fluid flow rate of the fresh fluid flowing out of the balancing unit, and (c) a continuous flow rate of fluid through the filter unit is maintained if the fluid flow rate of the fresh fluid flowing out of the balancing unit is discontinuous, wherein each recirculation and balancing chamber comprises a single common entrance and exit for moving fresh fluid and used fluid into and out of the chamber.

12. The method of claim 1, wherein each recirculation and balancing chamber comprises a single common entrance and exit for moving fresh fluid and used fluid into and out of the chamber.

* * * * *